United States Patent [19]

Carenzi et al.

[11] Patent Number: 5,200,396
[45] Date of Patent: Apr. 6, 1993

[54] METHOD OF TREATING NEURODEGENERATIVE DISORDERS USING EPIDERMAL GROWTH FACTOR

[75] Inventors: Angelo Carenzi, Busto Arsizio; Gianni Pezzoli, Milan; Sante Ricciardi, Bresso, all of Italy

[73] Assignee: Zambon Group S.P.A., Vicenza, Italy

[21] Appl. No.: 690,670

[22] Filed: Apr. 24, 1991

[30] Foreign Application Priority Data

Apr. 26, 1990 [IT] Italy ................................ 20144 A/90

[51] Int. Cl.⁵ ...................... A61K 37/02; A61K 37/36
[52] U.S. Cl. ........................................ 514/12; 514/2; 514/21
[58] Field of Search ................................ 514/2, 12, 21

[56] References Cited

U.S. PATENT DOCUMENTS 4,861,757  8/1989  Antoniades .......................... 514/21

FOREIGN PATENT DOCUMENTS 0267015  5/1988  European Pat. Off. .
0357240  3/1990  European Pat. Off. .
0364266  4/1990  European Pat. Off. .
0412554  2/1991  European Pat. Off. .
2223033  10/1974  France .
8602271  4/1986  World Int. Prop. O. .
9011781  10/1990  World Int. Prop. O. .

OTHER PUBLICATIONS

J. Biol. Chem., vol. 237, No. 5, May 1962, pp. 1555-1562, Cohen, "Isolation of a Mouse Submaxillary Gland Protein . . . ".
J. Biol. Chem., vol. 247, No. 23, 1972, pp. 76097611, Savage et al, "Epidermal Growth Factor and a New Derivative" Levodopa-Merck Index, XI Ed., No. 5344, p. 860.

*Primary Examiner*—F. T. Moezie
*Attorney, Agent, or Firm*—Stevens, Davis, Miller & Mosher

[57] ABSTRACT

Described are pharmaceutical compositions containing neurotrophically effective amount of Epidermal Growth Factor (EGF) as active ingredient together with pharmaceutical excipients and their use in the method of treatment of neurodegenerative disorders, such as Parkinsonism and disorders of traumatic origin.

3 Claims, No Drawings

METHOD OF TREATING NEURODEGENERATIVE DISORDERS USING EPIDERMAL GROWTH FACTOR

FIELD OF THE INVENTION

The present invention relates to pharmaceutical compositions containing Epidermal Growth Factor as active ingredient useful in the treatment of neurodegenerative disorders such as, for example, Parkinson's disease or disorders of traumatic origin.

Epidermal Growth Factor (EGF) is a natural protein existing both in human and in mammals which has a stimulating activity on the cell proliferation of epithelial tissue and so accelerates the healing of ulcers of various origin.

DESCRIPTION OF RELATED ART

At first EGF was identified and isolated from the mouse submaxillary glands [J. Biol. Chem., 237, 1555, (1962)].

The analysis of the protein showed the presence of 53 aminoacids with three disulfide bonds. Generally, this protein is indicated as mouse-EGF or more shortly "m-EGF".

The different methods for separation and purification of m-EGF or some suitable enzymatic treatments can result in obtaining a protein in which 2 or 5 terminal aminoacids are lost [J. Biol. Chem., 247, 7609, (1972)]. These derivatives, which are called "EGF-2" and "EGF-5" respectively, show properties analogous to EGF with 53 aminoacids.

EGF is also present in different human biological liquids such as plasma, saliva, urine, amniotic liquid and milk.

Human EGF or more shortly "h-EGF" is a protein having substantially the same physico-chemical characteristics and biological activity of m-EGF.

For these reasons, from now on, the term EGF includes m-EGF as well as EGF-2, EGF-5 and h-EGF or mixtures thereof.

The stimulating activity on the proliferation of epithelial tissue and, more generally, the mitogenic activity has suggested the use in human therapy to enhance epidermal and corneal healing for instance in case of ulcers and oculistic surgery.

Parkinson's disease is a neurodegenerative disease of the central nervous system which affects about 1-2% of people aged over 60 and which is characterized by a constant depigmentation of the substantia nigra due to a neuronal depauperation of this mesencephalic nucleus.

Other neurodegenerative disorders are disease related to cerebral traumas such as traumas due to car crashes or similar accidents.

The world incidence of nervous parenchima effects due to cranial penetrating traumas is extremely high and related to the rate of industrialization and motorization of the considered country. In Europe and in the U.S.A., head traumas represent the main cause of severe motor deficiencies in young people.

These motor deficiencies have substantially the symptoms generally known as parkinsonism.

At present, only symptomatic therapies such as the therapies with dopaminergic agonists are available for the treatment of Parkinson's disease or of parkinsonism. Levodopa (Merck Index XI Ed., No. 5344, page 860), the most used drug, is able to partially restore the mesencephalic-striatal level of dopamine.

Nevertheless, the therapy with levodopa has several limitations which can be summarized in a choreic-akinetic syndrome appearing after about five years from the beginning of the use of the drug.

In fact, the patient, who has lost substantially all the neurons of the substantia nigra, which neurons transform levodopa into dopamine, less and less responds to the drug. As a consequence, the patient has a feeling of well-being for a progressively shorter time and shows fluctuations in the daily motory performance, that is hyperkinesia during the phase of efficacy of the drug (chorea) and akinesia (motory block) when the plasmatic levels of the drug are low.

The use of slow-release pharmaceutical compositions containing levodopa did not substantially change patient conditions with respect to the chronic treatment.

The use of drugs able to directly stimulate the receptor has not even shown to be better than the therapy with levodopa.

During the last years some growth factors, and particularly NGF (Nerve Growth Factor), have shown to be able to act as trophic factors towards some neuronal types, promoting neuronal cell survival as well as neurite outgrowth in rat brain cells.

SUMMARY OF THE INVENTION

We have now surprisingly found that EGF is able to restore, at least partially, in vivo the functionality of the dopaminergic system and therefore it is useful in the therapeutic treatment of neurodegenerative disorders of the central nervous system and, in particular, of Parkinson's disease and of parkinsonism.

Therefore, pharmaceutical compositions containing a neurotrophically active amount of EGF, optionally in admixture with a pharmaceutically acceptable carrier, which are useful in the treatment of neurodegenerative disorders, are the object of the present invention.

DESCRIPTION OF THE PREFERRED EMBODIMENTS

A further object of the present invention is a method for the treatment of neurodegenerative disorders and, in particular, of Parkinson's disease and of parkinsonism, comprising the administration of a neurotrophically effective amount of EGF.

Preferably, the pharmaceutical compositions object of the present invention are in the form of injectable solutions or of freeze-dried powders from which injectable solutions are obtained by dilution at the moment of use.

The injectable solutions, optionally prepared at the moment of use by dilution of a freeze-dried powder, object of the present invention, are particularly suitable for intracerebroventricular administration using osmotic minipumps.

Examples of such minipumps are those commercialized as "Alzet 2002 ®" (trademark of Alza Corp.).

Furthermore, when EGF is administered by a route different from the intracerebroventricular route, the use of suitable administration systems containing EGF such as liposomes or nano-particles may be preferred, in order to allow a higher amount of EGF to cross the blood-brain barrier.

The in vivo efficacy of EGF in the treatment of neurodegenerative disorders has been evaluated in rodents by studying, before and after EGF treatment, the change in the rotational behaviour of the animal to which a lesion of the nigrostriatal pathway was surgically effected [Acta Physiol. Scand., Suppl. 367, 69, (1971)] (see Example 1). This experimental model is an art-recognized model and it is considered to be predictive in studying the efficacy of drugs in the treatment of parkinsonisms.

It is worth noting that, in this experimental model, other neurotrophic factors resulted to be inactive.

For example, NGF did not show, in practice, any efficacy in changing the rotational behaviour of the animal [Brain Research, 459, 398, (1988)].

The compositions object of the present invention contain a neurotrophically effective amount of EGF together with pharmaceutical excipients. In particular, suitable excipients are those useful for the preparation of injectable formulations and freeze-dried powders or of pharmaceutical formulations such as liposomes, or protein stabilizing agents.

The preparation of the compositions is carried out according to traditional techniques bearing in mind, of course, that EGF is a protein.

The amount of EGF to be administered to the patient depends on several factors such as the seriousness of the neurodegenerative disease, the individual response of the patient, associated therapies, the selected pharmaceutical formulation and the selected administration route. Generally the daily dose of EGF for the method of treatment according to the present invention is between 0.05 and 30 µg. In case of intracerebroventricular administration, solutions containing an EGF concentration between 0.1 and 10 mg/l will be administered.

In order to better illustrate the present invention, the following examples are now given.

EXAMPLE 1

To a group of Sprague Dowley rats weighing about 200 grams a lesion of the nigrostriatal pathway was surgically effected.

After about two weeks, the animals were selected on the basis of the number of rotations in one direction after dopaminergic stimulation, indicative of a lesion of the nigrostriatal pathway. For this purpose, the rats were treated with amphetamine (0.5 mg/kg i.p.) and put into apparatus able to monitor the number of rotations homolateral to the lesion.

About 40 days after the lesion, the rats were randomized into two groups showing the same number of rotations. Osmotic minipumps were subcutaneously inserted at intra-scapular level.

Shortly before the use, the minipumps "Alzet 2002 ®" were filled with a saline solution (200 µl) containing bovine serum albumin fraction V (BSA) 0.1% (Fluka) and EGF (0.6 µg) for each group of treated animals, whereas a saline solution containing BSA only was administered to the control animals.

The minipumps were inserted according to the technique described by Jankovic J. in South Med. J., 81(8), August 1988, 1021-7.

In order to realize an infusion for 28 days, it was necessary to substitute the minipumps with other minipumps containing a fresh EGF solution after 14 days.

At the end of the infusion, the rats were tested by subcutaneous administration of amphetamine (0.5 mg/kg) every 10 days in order to evaluate the rotational behaviour in comparison with the rotational behaviour, under the same conditions, of not treated lesioned rats. The not treated lesioned rats showed, in behavioural tests carried out after about 2 months from the end of the infusion, an average rotation number of $98 \pm 20$ (14 animals) while the EGF-treated lesioned rats showed an average rotation number of $45 \pm 11$ (11 animals) ($p \geq 0.05$ student t).

These results show that the lesioned animals, which have received EGF, progressively reduced their rotational activity in response to amphetamine; this is indicative of a progressive restoration of the functionality of the previously lesioned nigrostriatal pathway [Nature, 292, 351, (1981); Science, 204, 643, (1979)].

EXAMPLE 2

The experimental model described in Example 1 is usually referred to as "experimental parkinsonism" in the medical literature.

Since the nigrostriatal lesion is performed with neurosurgical procedures, the motor asymmetry induced in rats, according to Example 1, corresponds to an effect of cranial penetrating traumas. Indeed, the most varied motor syndromes related to cerebral traumas also including parkinsonisms are described in human pathology.

It follows that the efficacy of EGF, demonstrated on the experimental parkinsonism as reported in Example 1, can be considered also useful for lacerated cranial wounds, in particular for those involving the extrapyramidal system.

EXAMPLE 3

After the rotational behaviour studies as described in example 1, the animals were sacrificed after about 3 months from the infusion and the brains were studied by an immunohystochemical method in order to evaluate the amount of tyrosine hydroxylase enzyme (TH) present in the nigrostriatal pathways [Istochemie, 33, 231, (1973); J. Histochem., 25, 1222, (1977)].

The presence of TH is a recognized sign of the functionality of dopaminergic nigrostriatal neurons.

Assuming equal to 100% the TH value present in the not lesioned nigrostriatal pathways, the TH amount in the lesioned nigrostriatal pathways of the not EGF-treated animals was 22%.

On the contrary, in the lesioned nigrostriatal pathways of the EGF-treated animals, the TH amount was 78%.

In addition, counts of TH-positive neurons in the substantia nigra, starting point of the nigrostriatal pathway, were carried out on each brain.

In the EGF-treated lesioned animals, the number of neurons resulted to be about three times higher than that of the not treated lesioned animals.

EXAMPLE 4

EGF does not easily cross the blood-brain barrier.

Pharmaceutical technology has provided administration systems, like liposomes or nano-particles, suitable for increasing the penetration of drugs through the blood-brain barrier.

When it is desired to administer EGF orally or intravenously in the method of treatment of parkinsonisms according to the present invention, prudence suggests the use of such systems for administering EGF.

Accordingly, the preparation of liposomes containing EGF can be carried out following the technologies described, for example, in "Biodegradable Polymers as Drug Delivery Systems—Chapter 8—Liposomes—Edited by Mark Chasin and Robert Langer—Marcel Dekker Inc.—New York 1990" and references cited therein.

The preparation of nano-particles, which can be called also microspheres, containing EGF can be carried out according to the procedure described, for example, in U.S. Pat. No. 4,147,767 (hereby incorporated by reference).

What we claim is:

1. A method for the treatment of neurodegenerative disorders in a patient comprising administering to said patient in need of the treatment a neurotrophically effective amount of Epidermal Growth Factor.

2. A method according to claim 1 wherein the patient has Parkinson's disease.

3. A method according to claim 1 or 2 wherein Epidermal Growth Factor is administered in an amount from 0.05 to 30 µg/day.

* * * * *